United States Patent
Platzek et al.

(10) Patent No.: US 12,358,877 B2
(45) Date of Patent: Jul. 15, 2025

(54) SYNTHESIS OF 4-AMINO-5-METHYL-1H-PYRIDIN-2(1H)-ON (INTERMEDIATE COMPOUND FOR THE SYNTHESIS OF THE MR ANTAGONIST FINERENONE) FROM 2-CHLORO-5-METHYL-4-NITRO-PYRIDINE-1-OXIDE USING THE INTERMEDIATE COMPOUND 2-CHLORO-5-METHYL-4-PYRIDINAMINE

(71) Applicants: Bayer Aktiengesellschaft, Leverkusen (DE); Bayer Pharma Aktiengesellschaft, Berlin (DE)

(72) Inventors: Johannes Platzek, Berlin (DE); Kai Lovis, Düsseldorf (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 949 days.

(21) Appl. No.: 17/435,606

(22) PCT Filed: Feb. 28, 2020

(86) PCT No.: PCT/EP2020/055292
§ 371 (c)(1),
(2) Date: Sep. 1, 2021

(87) PCT Pub. No.: WO2020/178175
PCT Pub. Date: Sep. 10, 2020

(65) Prior Publication Data
US 2022/0153699 A1    May 19, 2022

(30) Foreign Application Priority Data
Mar. 5, 2019  (EP) ..................................... 19160904

(51) Int. Cl.
*C07D 213/73* (2006.01)
(52) U.S. Cl.
CPC .................................. *C07D 213/73* (2013.01)
(58) Field of Classification Search
CPC .................................................. C07D 213/73
See application file for complete search history.

(56) References Cited

FOREIGN PATENT DOCUMENTS

| CN | 1311185 A | * | 9/2001 |
| CN | 103193704 A | * | 7/2013 |
| CN | 103420902 A | * | 12/2013 |
| WO | 2005/100342 A1 | | 10/2005 |
| WO | 2008/104306 A2 | | 9/2008 |
| WO | 2016/016287 A1 | | 2/2016 |

OTHER PUBLICATIONS

Beak "Equilibration Studies. Protomeric Equilibria of 2- and 4-Hydroxypyridines, 2- and 4-Hydroxypyrimidines, 2- and 4-Mercaptopyridines, and Structurally Related Compounds in the Gas Phase" J. Am. Chem. Soc. 1976, 98, 1, 171-179.*
Greco "Comprehensive Organic Chemistry Experiments for the Laboratory Classroom" 2017 translated from 2011 Portuguese language edition, edited by Carlos A M Afonso, RSC publishing, p. 61.*
White, Nicholas A. "4-nitropyridine N-oxide" in e-EROS Encyclopedia of Reagents for Organic Synthesis, (2016), 1-3.*
Freifelder Practical Catalytic Hydrogenation Techniques and Applications Wiley: New York 1971, 1-83, discussion on pp. 9-11.*
Tafesh et. al. "A Review of the Selective Catalytic Reduction of Aromatic Nitro Compounds into Aromatic Amines, Isocyanates, Carbamates, and Ureas Using CO" Chemical Reviews 1996, 96, 2035-2052.*
International Search Report and Written Opinion of PCT/EP2020/055292, filed Feb. 28, 2020 by Bayer Aktiengesellschaft, issued by the European Patent Office on Jul. 15, 2020.
Bärfacker, L. et al., "Discovery of BAY 94-8862: A Nonsteroidal Antagonist of the Mineralcorticoid Receptor for the Treatment of Cardiorenal Diseases," ChemMedChem, 2012, 7, 1385-1403.
Abbot, S.C. et al., "Synthesis of Heteroaryl-Fused Pyrazoles as P38 Kinase Inhibitors," Heterocycles, 2009, vol. 78, No. 11, 2811-2826.
Hung, N.C. et al., "A General Route to 5- and 6-Substituted 4-Amino-2-oxo-1,2-dihydropyridines," Synthesis, 1984, 765-766.
Searls, T. et al., "Synthesis of the Analogue Nucleoside 3-Deaza-2'-deoxycytidine and its Temple Activity with DNA Polymerase," Tetrahedron, 1999, 55, 11985-11996.

* cited by examiner

*Primary Examiner* — David K O'Dell
(74) *Attorney, Agent, or Firm* — Quarles & Brady LLP

(57) ABSTRACT

The present invention relates to a novel and improved method for preparing 4-amino-5-methylpyridone of the formula (I)

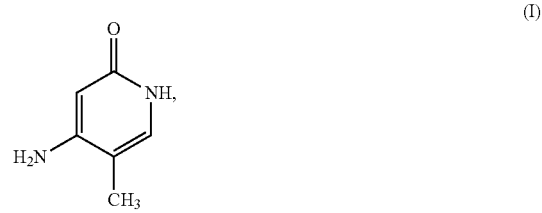

(I)

which is an intermediate in the preparation of the MR antagonist finerenone.

12 Claims, No Drawings

SYNTHESIS OF 4-AMINO-5-METHYL-1H-PYRIDIN-2(1H)-ON (INTERMEDIATE COMPOUND FOR THE SYNTHESIS OF THE MR ANTAGONIST FINERENONE) FROM 2-CHLORO-5-METHYL-4-NITRO-PYRIDINE-1-OXIDE USING THE INTERMEDIATE COMPOUND 2-CHLORO-5-METHYL-4-PYRIDINAMINE

This application is a U.S. national stage entry under 35 U.S.C. § 371 for International Application No. PCT/EP2020/055292, filed Feb. 28, 2020, the contents of which are incorporated herein by reference in its entirety, which claims priority to European Patent Application No. 19160904.9, filed Mar. 5, 2019.

The present invention relates to a novel and improved method for preparing 4-amino-5-methylpyridone of the formula (I)

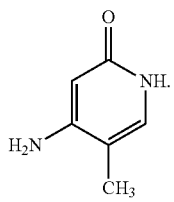
(I)

4-Amino-5-methylpyridone of the formula (I) is prepared by reacting chloro-methyl-aminopyridine (2) with KOH in methanol in an autoclave at elevated temperature.

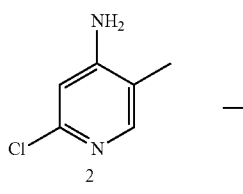

The invention also relates to a method for preparing chloro-methyl-aminopyridine (2)

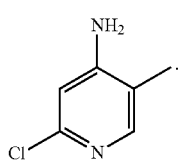
2

In the method, the nitro-N-oxide of the formula (3)

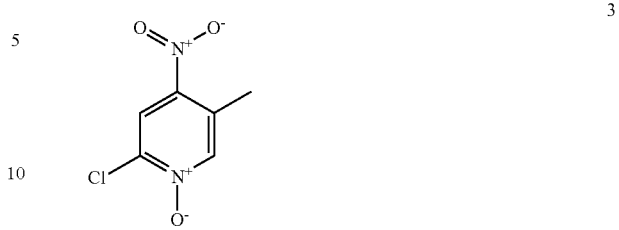
3 is hydrogenated on a platinum catalyst, yielding chloro-methyl-aminopyridine (2). With the method of the invention it is possible, starting from the nitro-N-oxide (3), to prepare via two chemical steps the target compound (I) in an overall yield of 84% in high purity (>99%).

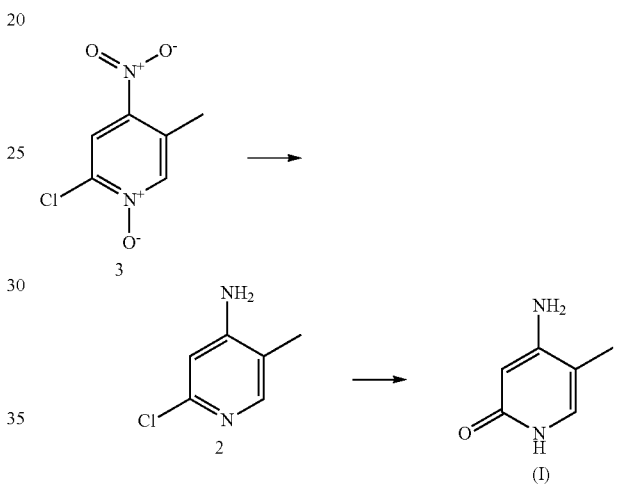

The compound of the formula (I) is a key intermediate for the preparation of finerenone (II):

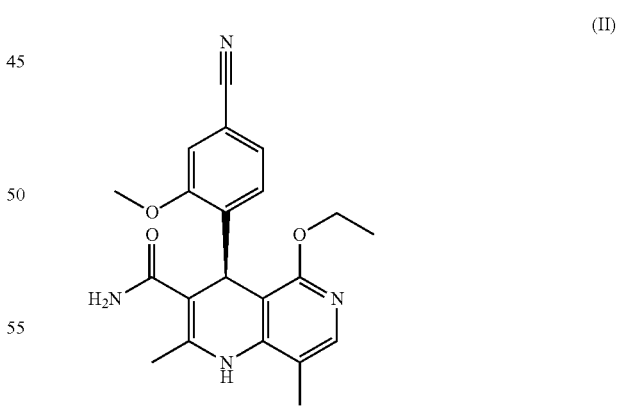
(II)

Finerenone (II) acts as a nonsteroidal antagonist of the mineralocorticoid receptor and can be used as an agent for the prophylaxis and/or treatment of cardiovascular and renal disorders such as heart failure and diabetic nephropathy.

The compound of the formula (II) and the process for the preparation thereof are described in WO 2008/104306 and ChemMedChem 2012, 7, 1385 and also in WO 2016/016287 A1 (Bayer Pharma AG), both publications disclosing a detailed discussion of the research synthesis. A disadvantage of the synthesis described therein is the fact that this synthesis is unsuitable for a further industrial-scale process, since many steps proceed at very high dilution, with very high excesses of reagents, and therefore in a relatively low yield overall.

There was accordingly a need for a synthesis that can be executed on an industrial scale and that reproducibly affords the process intermediate of the formula (I) in high overall yield, with low production costs and in high purity, and that meets all regulatory requirements, in order to supply clinical trials with active substance and for use in subsequent regulatory submissions.

The preparation of compound (I) is described in Synthesis, p. 765 (1984) (Example 3c). Starting from malonyl chloride and propionitrile, the chloropyridine hydrochloride is obtained in a yield of 40% of theory, which is then directly hydrogenated with Pd/C: 86% of theory. The overall yield over the two steps is 34.4% of theory.

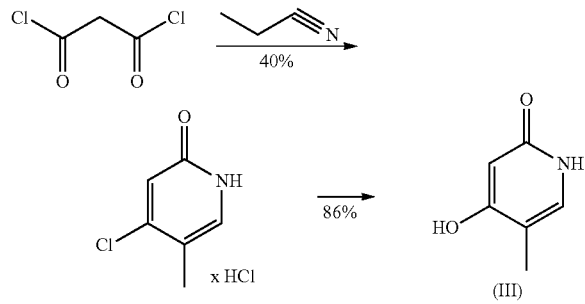

Starting from hydroxypyridone (III), which is described in Example 1c of the publication in Synthesis, reaction in boiling benzylamine (IV) affords compound (V). The benzyl group in compound (V) is then hydrolytically cleaved by catalytic hydrogenation over palladium/carbon. The overall yield over the two steps is 62.4% of theory.

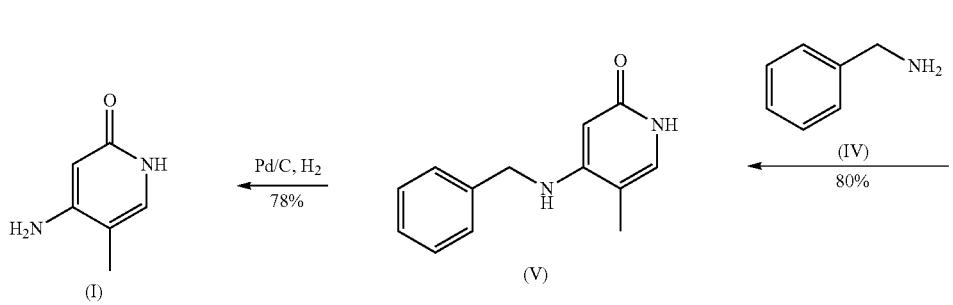

A disadvantage of the method is the use of a very large excess of benzylamine: for 30 mmol of the compound of the formula (III), 30 ml (275.2 mmol) is used, which is a 9.17-fold excess based on compound (III). The recycling of excess benzylamine is laborious and associated with considerable costs. The reaction is carried out in boiling benzylamine (185° C.), the reaction time is 36 hours. Such high temperatures are not practicable in standard stirred apparatuses and require special technical equipment. On repeating the procedure, by-product (VI) was in particular observed, which is attributable to traces of palladium from the precursor for (III):

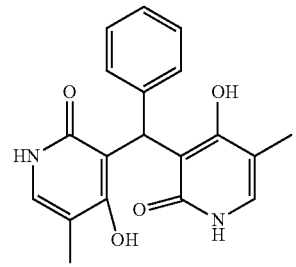

Under the harsh reaction conditions, dehydrogenation to benzylimine occurs, which then decomposes to benzaldehyde (water is formed during the reaction), the benzaldehyde condensing with the compound of the formula (III) to form the compound of the formula (VI). This by-product forms particularly on scale-up of the batches (up to >10%) and is carried over as far as the compound of the formula (I). The reaction solution is worked up by cooling to room temperature, washing the precipitated crystals with methyl ethyl ketone and o-dichlorobenzene and then recrystallizing from o-dichlorobenzene. Here too, it would be advantageous to dispense with chlorinated solvents and pursue more environmentally friendly variants.

The subsequent debenzylation takes place in glacial acetic acid, 10 mmol in 200 ml, which is 2.14 g of compound (V) in 200 ml. This corresponds to a 93.45-fold excess, which means that, for 1 kg of (V), 93.45 L of acetic acid would be required. These are huge excesses that are out of the question for an industrial process. Moreover, for the conversion of 10 mmol of (V), 600 mg of Pd catalyst on carbon (10% and 30%) is used. This means that, in order to debenzylate 1 kg of compound (V), 280 g of catalyst would be necessary. This too is impractical from an industrial and economic viewpoint. For workup, the catalyst is filtered off and the filtrate evaporated to dryness, traces of acetic acid are removed by azeotroping with toluene and the residue is taken up in acetone or methyl ethyl ketone and filtered. This process is technically not feasible when upscaling, since stirred apparatuses do not evaporate to dryness. Furthermore, three different solvents are needed for the isolation. The strongly coloured reaction product is then further purified by chromatography (dichloromethane/MeOH 1:1), which is something else that would if possible need to be avoided in an industrial-scale process. The overall yield over 4 chemical steps, starting from malonyl chloride, is 21.4% of theory.

The problem addressed by the present invention was that of developing an alternative synthesis for the process intermediate 4-amino-5-methylpyridone as an intermediate for the preparation of the compound of the formula (II), finerenone, in particular a method that is readily executable on an industrial scale, is cost-effective and avoids large excesses of solvent, and uses reagents that are more environmentally friendly.

With the present invention, a very efficient synthesis has been found that allows the disadvantages mentioned above to be circumvented. Starting from the chloro-methyl-aminopyridine (2) known in the literature

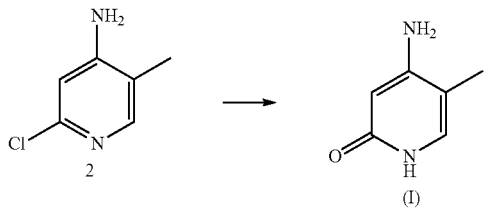

the target compound (I) is obtained by reacting compound (2) in an autoclave at elevated temperature under either acidic or basic conditions. A similar reaction with NaOH in methanol is described in Tetrahedron 55 (1999), p. 11 985. The product is purified by chromatography. Unfortunately the reaction of compound 2 under these conditions afforded a mixture of target compound (I) and the 2-methyl ether (7):

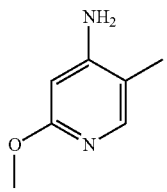

This mixture could be separated only by chromatography.

Surprisingly, the conversion into the target compound proceeds very smoothly when potassium hydroxide (KOH) is used instead of sodium hydroxide. Then the reaction also proceeds in methanol as solvent without the methyl ether (7) being obtained as a by-product. Preference is given to using pure methanol as solvent, but it is also possible to use aqueous methanol. The reaction is carried out in an autoclave at temperatures of 160 to 200° C., preferably at 180° C. Reaction times are 15-48 hours, depending on the chosen temperature, i.e. inter alia the reaction times tend to be shorter at higher temperatures. For workup, the reaction mixture is neutralized (to approx. pH 7) with a mineral acid, for example hydrochloric acid, sulfuric acid or phosphoric acid, preferably hydrochloric acid, and then concentrated to small volume and water removed azeotropically by adding to ethanol. Finally, it is redistilled in methanol and the salts are filtered off. It is concentrated to small volume and redistilled on water. For recrystallization, it is concentrated to about three times the amount by volume (based on starting material 2). After cooling to 0° C., the product is isolated, for example by filtration, washed if necessary with a little cold water and dried under reduced pressure at elevated temperature (30-70° C.).

The present invention accordingly provides a method for preparing the process intermediate 4-amino-5-methylpyridone of the formula (I), characterized in that chloro-methyl-aminopyridine (2) is reacted with KOH in methanol in an autoclave.

In a preferred embodiment, the method is executed at temperatures of 160° C. to 200° C., in particular at 180° C.

A further aspect of the invention is a novel method for preparing chloro-methyl-aminopyridine (2):

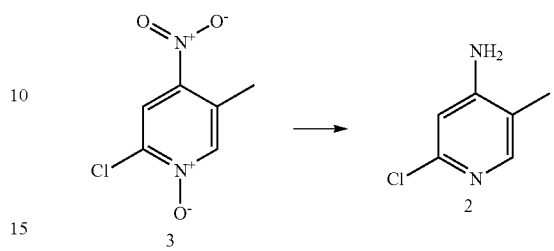

In this method, the use of a Pt catalyst reduces the nitro group and the nitro-N-oxide at the same time. A catalytic hydrogenation reaction of this kind, in a pyridine having a substitution pattern of this kind, is as yet undescribed in the literature.

The preparation of compound 2 is known from the literature (WO 2005/100342 A1), the desmethyl compound of 2 is likewise known and is prepared by similar methods (Tetrahedron 55 (1999), p. 1195), but the industrial-scale transfer (upscaling) of the methods described therein is difficult, since they include working with elemental zinc or iron under acidic conditions, preferably acetic acid. The use of Raney nickel as hydrogenation catalyst is likewise possible, but upscaling is problematic, since Raney nickel wastes are extremely pyrophoric. Moreover, the industrial execution is also a safety challenge, since the strong exothermicity means that the reaction is not easy to control. Furthermore, workup becomes very difficult and laborious and on top of that generates a lot of metal salt waste that must be disposed of, which is not inconsequential when producing such products on the ton scale.

A commonly occurring side reaction in the reduction of 2-chloro-substituted pyridine derivatives is the concomitant reduction of the chlorine atom to hydrogen (compound 4).

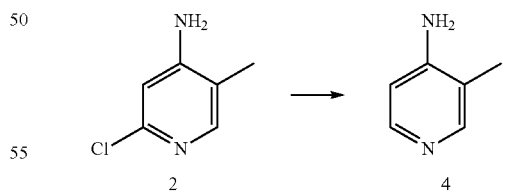

This side reaction is absent in this novel inventive method or observed only to a very minor degree (<<1%), which would therefore be surprising and unexpected to those skilled in the art. The reaction is preferably carried out in protic solvents, for example alcohols such as ethanol, methanol, isopropanol, n-propanol and n-butanol. It is however also possible to use solvents such as THF, dioxane and 2-methyl-THF. In some cases, the addition of water can be advantageous.

The catalyst used is preferably a platinum-containing catalyst. The following platinum catalysts may be used:

---
0.8% Pt + 0.6% Mo on carbon powder
1% Pt + 2% V on carbon powder
0.5% Pt + 0.3% Mo on carbon powder
---

Particular preference is given to using 0.8% Pt+0.6% Mo on carbon powder (from BASF). The hydrogen pressure during the hydrogenation should be between 2 and 7 bar, preferably 2 and 5 bar, more preferably 3 bar. The temperature should be between 20 and 50° C., but preferably between 25 and 30° C., more preferably 30° C. The reaction time is 10 to 30 hours, preferably 18 to 22 h.

For isolation, the catalyst is filtered off and the solution concentrated to small volume and redistilled onto the solvent of the following reaction, preferably methanol. It is advantageous when the crude product is used directly in the following reaction. The reaction proceeds quantitatively.

The preparation of the nitro-N-oxide (3) is known from the literature, as described for example in Heterocycles, vol. 78, No. 11, 2009, p. 2811 or in WO 2005/100342 A1.

In Heterocycles, vol. 78, No. 11, 2009 the following yields for the preparation of compound 3 are described: overall yield of theory over 2 steps 64%.

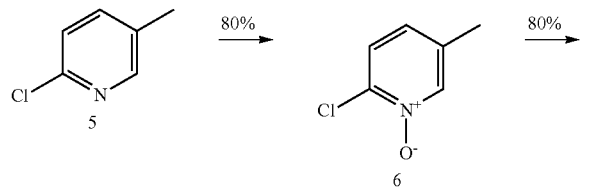

The present invention further provides a method for preparing the process intermediate chloro-methyl-aminopyridine (2) by hydrogenating nitro-N-oxide (3) on a platinum catalyst.

In a preferred embodiment, 0.8% platinum (Pt)+0.6% molybdenum (Mo) on carbon powder is used as catalyst.

In a further preferred embodiment, 1% platinum (Pt)+2% vanadium (V) on carbon powder is used as catalyst.

In a further preferred embodiment, 0.5% platinum (Pt)+ 0.3% molybdenum (Mo) on carbon powder is used as catalyst.

With the novel inventive method it is possible, starting from the nitro-N-oxide (3), to prepare via two chemical steps

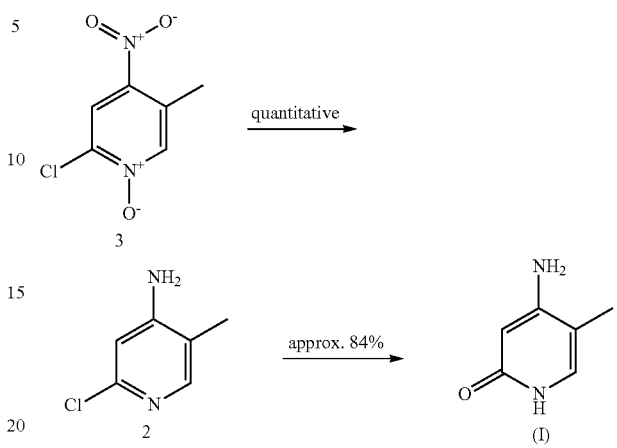

the target compound (I) in an overall yield of 84% in high purity (>99%). A further advantage of the method is that compound (2) can be converted into compound (I) directly, without further purification.

If the yields of the novel method are combined with those known from the literature, starting from the inexpensive and commercially very readily obtainable 2-chloromethylpyridine (5), an overall yield of 54% of theory is achieved, which is an approximately 2.5-fold improvement in yield compared with the prior art method described in Synthesis.

The present invention further provides a method for preparing the process intermediate 4-amino-5-methylpyridone of the formula (I), characterized in that the intermediate nitro-N-oxide (3) is first hydrogenated on a platinum catalyst and the resulting intermediate chloro-methyl-aminopyridine (2) then reacted with potassium hydroxide (KOH) in methanol in an autoclave.

The paragraphs that follow relate to embodiments of the invention:

1. Method for preparing the process intermediate 4-amino-5-methylpyridone of the formula (I)

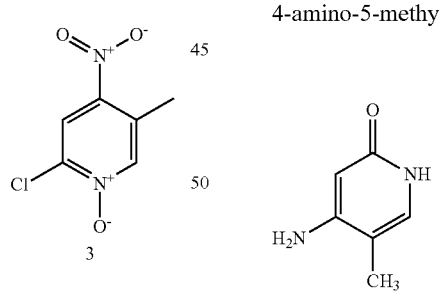

characterized in that chloro-methyl-aminopyridine (2)

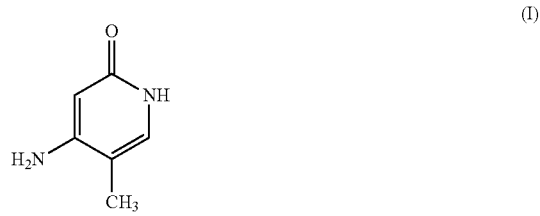

is reacted with KOH in methanol in an autoclave.

2. Method according to paragraph 1, characterized in that it is executed at temperatures of 160° C. to 200° C.
3. Method for preparing the process intermediate chloro-methyl-aminopyridine (2),

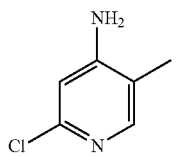

characterized in that nitro-N-oxide (3)

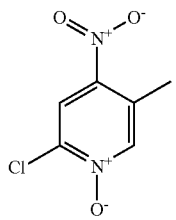

is hydrogenated on a platinum catalyst.
4. Method according to paragraph 3, characterized in that 0.8% platinum+0.6% molybdenum on carbon powder is used as catalyst.
5. Method according to paragraph 3, characterized in that 1% platinum+2% vanadium on carbon powder is used as catalyst.
6. Method according to paragraph 3, characterized in that 0.5% platinum+0.3% molybdenum on carbon powder is used as catalyst.
7. Method for preparing the process intermediate 4-amino-5-methylpyridone of the formula (I), characterized in that the nitro-N-oxide (3) intermediate is first hydrogenated on a platinum catalyst and the resulting chloro-methyl-aminopyridine (2) intermediate is then reacted with KOH in methanol in an autoclave.

EXAMPLES

Example 1 Preparation of 2-chloro-5-methylpyridin-4-amine (Compound 2)

A glass pressure reactor with cross-beam stirrer was charged under argon with 29 g (153.788 mmol) of 2-chloro-5-methyl-4-nitro-1-oxidopyridin-1-ium (compound 3, Heterocycles, vol. 78, No. 11, 2009, p. 2811) and 2.9 g of hydrogenation catalyst (0.8% Pt and 0.6% Mo on activated carbon (D505A-105 0.8% Pt+0.6% Mo on carbon powder, BASF) and 320 ml of ethanol were added. The reactor was closed and inertized three times, each time with 3 bar argon overpressure. Hydrogenation was then carried out for 20 hours at 30° C. under a 3 bar hydrogen overpressure (conversion >98%). The reactor was inertized with argon and the reaction solution filtered through 10 g of kieselguhr. The filtrate was concentrated to dryness under reduced pressure.
Yield: 23.0 g (quantitative, product still contained ethanol), purity: 97.5% (HPLC)
MS (EIpos): m/z=143 [M+H]+

1H-NMR (300 MHz, DMSO-d6): δ=1.96 (s, 3H), 6.16 (br s, 2H), 6.50 (s, 1H), 7.68 (s, 1H)
In an analogous manner, a conversion of approx. 98% was achieved with a catalyst consisting of 0.8% Pt and 0.3% Mo on activated carbon. Use of 1% Pt+2% V on activated carbon achieved a conversion of approx. 87%.

Example 2 Preparation of 4-amino-5-methyl-1H-pyridin-2-one (I)

A pressure reactor was charged with 4.0 g of the title compound from Example 1 (compound 2) in 40 ml of methanol and 12.5 g of potassium hydroxide (KOH) was added. This was then heated to 180° C. for 16 hours (rise in pressure to 12.5 bar). It was allowed to cool.
The reaction was carried out 5 times with in each case 4.0 g of the title compound from Example 1 and the reaction solutions combined after cooling.
Workup: The mixture was adjusted to pH 7.0 with approx. 100 ml of aq. 25% hydrochloric acid while cooling, then evaporated to dryness under reduced pressure, and the residue azeotroped 5 times with ethanol, each time with 50 ml (evaporated to dryness under reduced pressure to remove traces of water). 400 ml of methanol was added to the evaporation residue and the mixture was stirred. The salt (KCl) was filtered off and washed with two 25 ml portions of methanol. The filtrate was concentrated to dryness under reduced pressure. The evaporation residue was recrystallized from 60 ml of water. After cooling to 0° C., the precipitated crystals were filtered off. The wet product was then dried under reduced pressure at 30° C.
Yield: 13.5 g (77.53% of theory); purity according to HPLC: 99.1%
A further 1.10 g (6.32% of theory) was isolated from the mother liquor, thereby achieving an overall yield of approx. 84% of theory.
MS (EIpos): m/z=125 [M+H]+
1H-NMR (300 MHz, DMSO-d6): δ=1.81 (s, 3H), 2.54 (s, 1H), 5.24 (s, 1H), 5.79 (s, 2H), 6.85 (s, 1H), 10.27 (br s, 1H)
From what has been described above, it is clear that the methods available up to now have the disadvantages that
(1) a multistep synthesis is carried out,
(2) the by-products of the formula (VI) (up to >10%), of the formula (4) and/or of the formula (7) are formed, which occur as impurities in the preparation of the compound of the formula (I) and need to be removed by laborious chromatographic processes,
(3) benzylamine is used in a very large excess, the recycling of which is laborious and associated with considerable costs,
(4) the reaction needs to be carried out in boiling benzylamine at 185° C. and with a reaction time of 36 hours, since such high temperatures are not practicable in standard stirred apparatuses and require special technical equipment,
(5) chlorinated solvents are used, which are not environmentally friendly, and
(6) large amounts of Pd catalyst on carbon need to be used, the separation and processing of which is not only laborious, but also scarcely practicable in an industrial-scale synthesis.
By contrast, the method of the invention avoids these disadvantages and achieves the following effects and advantages:
(1) the method/synthesis needs fewer steps in order to afford the compound of the formula (I) or the compound of the formula (2), (2) the compound of the formula (I) is obtained in high purity directly, without purification, (3) the compounds of the formulas (VI), (4) and/or (7) do not form as undesired by-products, (4) chromatographic separation, as is described in the prior art, is not required, thus making this novel inventive method very attractive as regards upscaling for production on a large scale, (5) the repeated use of solvents, in particular chlorinated solvents, can be eliminated in part or altogether, making the method of the invention much more environmentally friendly and (6) much lower reaction times and/or lower reaction temperatures are required.

Overall, the method of the invention represents a very efficient, shorter synthesis without the use of chromatography, that is also suitable for upscaling. With the method of the invention it was possible, starting from the nitro-N-oxide (3), to prepare via two chemical steps the target compound (I) in an overall yield of 84% in high purity (>99%).

The invention claimed is:

1. A method for preparing the process intermediate 4-amino-5-methylpyridone of the formula (I)

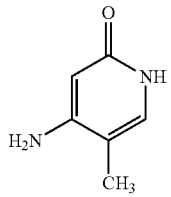

comprising reacting chloro-methyl-aminopyridine (2)

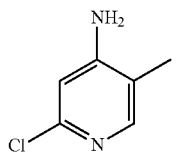

with KOH in methanol in an autoclave.

2. The method according to claim 1, wherein the reaction is carried out at a temperature within a range from 160° C. to 200° C.

3. A method for preparing the process intermediate chloro-methyl-aminopyridine (2)

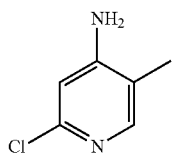

comprising hydrogenating a nitro-N-oxide of the formula (3)

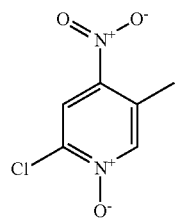

on a platinum catalyst.

4. The method according to claim 3, wherein 0.8% platinum and 0.6% molybdenum on carbon powder is used as the platinum catalyst.

5. The method according to claim 3, wherein 1% platinum and 2% vanadium on carbon powder is used as the platinum catalyst.

6. The method according to claim 3, wherein 0.5% platinum and 0.3% molybdenum on carbon powder is used as the platinum catalyst.

7. A method for preparing the process intermediate 4-amino-5-methylpyridone of the formula (I)

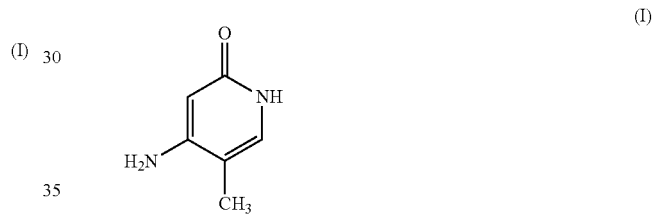

comprising the following steps a) and b):

a) hydrogenating a nitro-N-oxide of the formula (3)

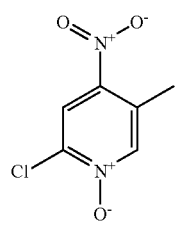

on a platinum catalyst, affording chloro-methyl-aminopyridine of the formula (2)

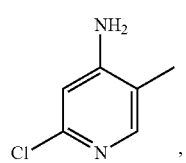

and b) reacting the resulting intermediate chloro-methyl-aminopyridine of the formula (2) with KOH in methanol in an autoclave.

8. The method according to claim 7, wherein 0.8% platinum and 0.6% molybdenum on carbon powder is used as the platinum catalyst in step a).

9. The method according to claim 7, wherein 1% platinum and 2% vanadium on carbon powder is used as the platinum catalyst in step a).

10. The method according to claim 7, wherein 0.5% platinum and 0.3% molybdenum on carbon powder is used as the platinum catalyst in step a).

11. The method according to claim 7, wherein in step b) the reaction is carried out at a temperature within a range from 160° C. to 200° C.

12. The method according to claim 7, wherein in step b) the reaction is carried out at a temperature of 180° C.

* * * * *